US007986996B2

(12) United States Patent
Bell

(10) Patent No.: US 7,986,996 B2
(45) Date of Patent: Jul. 26, 2011

(54) PASSIVE MONITORING OF BIOELECTICAL SIGNALS AND ACTIVE ELECTRICAL ANESTHESIA STIMULATION

(76) Inventor: John O. Bell, Sandy, UT (US)

( * ) Notice: Subject to any disclaimer, the term of this patent is extended or adjusted under 35 U.S.C. 154(b) by 457 days.

(21) Appl. No.: 11/719,750

(22) PCT Filed: Oct. 21, 2005

(86) PCT No.: PCT/US2005/038256
§ 371 (c)(1),
(2), (4) Date: May 19, 2007

(87) PCT Pub. No.: WO2006/047449
PCT Pub. Date: May 4, 2006

(65) Prior Publication Data
US 2010/0160998 A1    Jun. 24, 2010

Related U.S. Application Data

(60) Provisional application No. 60/621,951, filed on Oct. 25, 2004.

(51) Int. Cl.
*A61N 1/36* (2006.01)
(52) U.S. Cl. .............. 607/45; 600/544; 600/545; 607/1; 607/2; 607/3

(58) Field of Classification Search .......... 600/544–545; 607/1–3, 45
See application file for complete search history.

(56) References Cited

U.S. PATENT DOCUMENTS

| | | | |
|---|---|---|---|
| 3,835,833 A | 9/1974 | Limoge | |
| 5,792,069 A | 8/1998 | Greenwald | |
| 6,032,072 A | 2/2000 | Greenwald | |
| 6,161,044 A | 12/2000 | Silverstone | |
| 6,505,079 B1 | 1/2003 | Foster | |
| 6,567,702 B1 * | 5/2003 | Nekhendzy et al. | 607/46 |
| 6,757,558 B2 | 6/2004 | Lange | |
| 6,801,803 B2 | 10/2004 | Veirtio-Oja | |
| 6,882,166 B2 | 4/2005 | Shambroom | |
| 6,904,322 B2 | 6/2005 | Katsnelson | |
| 2004/0097802 A1 * | 5/2004 | Cohen | 600/411 |
| 2005/0043774 A1 | 2/2005 | Devlin | |
| 2005/0203437 A1 | 9/2005 | Shambroom | |
| 2006/0241562 A1 * | 10/2006 | John et al. | 604/503 |

* cited by examiner

*Primary Examiner* — Niketa I Patel
*Assistant Examiner* — Rex Holmes
(74) *Attorney, Agent, or Firm* — James Sonntag

(57) ABSTRACT

Passive monitoring of bioelectric signals is made in the presence of active electrical anesthesia stimulation signal such that the bio-electric signals have interference artifacts from the active signal. The interference artifacts are determined and suppressed to produce a processed bio-electric signal from which can be derived quantitative values for evaluating the neurological state.

27 Claims, 6 Drawing Sheets

EAS Component Diagram

EAS Component Diagram

TCES Signal Timing

NSM Components

Basic Component Diagram

Preprocessed Signal Discrimination

Reconstituting Lost Signal
Portions

PASSIVE MONITORING OF BIOELECTICAL SIGNALS AND ACTIVE ELECTRICAL ANESTHESIA STIMULATION

CROSS REFERENCE TO RELATED APPLICATIONS

This application is an application under 35 USC 371 from Application PCT/US2005/038256 filed under the Patent Cooperating Treaty, international filing date 21 Oct. 2005, which application claims priority from U.S. Provisional Application 60/621,951, 25 Oct. 2004, which applications are hereby incorporated by reference.

FEDERAL RESEARCH STATEMENT (Not applicable)

BACKGROUND OF INVENTION

Definitions

Anesthesia: Anesthesia is a loss of bodily sensation and reflexes that is induced and maintained by means of pharmacological compounds and inhalants (anesthetic agents or drugs) that are administered to patients in accordance with standard medical protocols. Anesthesia has three components: 1. Narcosis—consciousness, 2. Analgesia—absence of sensitivity to pain, and 3. Areflexia—inhibition of muscle movement.

Electroencephalogram (EEG) signals: Low level electrical signals caused by brain activity. Specific EEG signal characteristics detected in certain cranial locations may be processed and used to provide indications of certain kinds of brain activity, including indications of various neurologic states Neurologic State Monitor (NSM): Any device, system, or process using passive detection of cranial electrical signals, including EEG and other bio-electrical measurements, and providing quantitative values for the purpose of evaluating the degree of narcosis, analgesia, and/or areflexia of persons or animals under the influence of anesthetic agents.

Electrical Anesthesia Stimulation (EAS): Any active cranial electrical stimulation device that is used to augment or potentiate the effect of various compounds used for the induction and maintenance of anesthesia. EAS devices are composed of a cranial Electrode Assembly connected to an EAS Signal Generator as, for example, shown in FIG. 1. The Signal Generator will frequently contain various EAS controls and displays.

Transcutaneous Cranial Electrical Stimulation (TCES): A well-documented and specific embodiment of EAS developed by French physician and scientist Dr. Aime Limoge. TCES is typical of most EAS systems in that it specifically affects the components of anesthesia. In numerous animal and human studies, TCES has demonstrated significant reductions in the quantities of anesthetic compounds required to maintain safe and effective anesthesia.

DESCRIPTION OF THE RELATED ART

Electrical Analgesia Stimulation (EAS)

Different forms of Electrical Analgesia Stimulation (EAS) are found in the literature under a variety of names, including Low Current Electrostimulation, Auricular Microstimulation, Cranial Electrotherapy Stimulation (CES), Electro-Acupuncture (EA) and others. However, only the Limoge Transcutaneous Cranial Electrical Stimulation (TCES) [Limoge, 1975] and Russian [Lebedev, 1988] EAS methods are considered effective enough to be used in clinical anesthesiology. Of the two, the Limoge TCES approach has substantially more documentation in the medical literature, including both animal and human studies. TCES is also supported by reports of considerable clinical use (tens of thousands of surgical procedures since 1980) in France without adverse effects.

Transcutaneous Cranial Electrical Stimulation (TCES)
General

The specific embodiment of EAS used for describing this invention is TCES, as developed by the French physician and scientist Dr. Aime Limoge. For purposes of general discussion about the invention, the two terms may be used interchangeably. Limoge TCES is well documented in the research literature, and there is a reasonable body of evidence attesting to its efficacy, particularly in regards to TCES's ability to augment, or potentiate, the effect of anesthetic agents. Specifically Limoge TCES has been shown to reduce the requirements for a variety of anesthetic agents by 25% to 80% during surgical procedures. For example, TCES has been shown to:

increase the potency of nitrous oxide in humans by 30-40% [Stanley, 1982 A, B];
  reduce the need for opiates during neuroleptanesthesia by 50-80% [Stanley, 1982 B];
  potentiate opioid-induced analgesia in rats [Dougherty, 1989]; and decrease minimum alveolar concentration (MAC) of halothane in rats [Mantz, 1992].

TCES has evolved from Limoge's research in the 1960s and 1970s. During the late 1970s Dr. Limoge conducted a multi-year series of electro-anesthesia research studies for the U.S. Army Medical Research and Development Command. These studies clearly document the efficacy of TCES for maintaining effective post-induction anesthesia with significantly reduced requirements for anesthetic agents (drugs and inhalants). The TCES anesthesia protocol does require pharmacological induction to achieve a significant intrasurgical effect on anesthesia.

Finally, TCES has been shown to facilitate rapid recovery from general anesthesia without side effects such as respiratory depression, nausea and vomiting, itching, urinary retention, and immunosuppression [Stinus, 1990; Katsnelson, 1987]. Furthermore, TCES modalities have been used successfully in the management of alcohol and opiate withdrawal states in awake patients [Auricombe, 1990; Krupitski, 1991]. Given such promising capabilities, it seems strange that the U.S. medical community has virtually ignored TCES, and EAS technology in general. This has been due, in part, to a lack of rigorous, independent EAS research studies in the U.S. Additionally, a proliferation of limited capability, quasi-medical, electrical stimulation devices tends to stigmatize serious EAS technology and research.

EAS Function

TCES and other EAS systems are thought to specifically affect the Analgesia and Areflexia components of anesthesia by stimulation of the thalamic area of the brain with repetitive electrical pulses to induce release of inhibitory neurotransmitters. Although the specific mechanisms of action are still debated, endorphins, serotonin, and norepinephrine are frequently implicated as possible mechanisms for the analgesic effect of TCES.

Like most other EAS systems that show efficacy in anesthesia, TCES employs a combination of high and low frequency signal components, as shown in FIG. 2. This is described in U.S. Pat. No. 3,835,833, issued to Limoge on Sep. 17, 1974, which is hereby incorporated by reference. TCES is applied to patients through a frontal cathode electrode attached with adhesives to the patient's forehead and a pair of anode electrodes similarly attached below the mastoid region behind the patient's ears.

Neurological State Monitoring

New technology has recently become available in the operating room to supplement conventional anesthesia monitoring which is based on subjective evaluation of certain physiological variables. The new technology is referred to here as "neurological state monitoring" or NSM. NSM is a passive system in that it does not normally pass a signal current from the device into or through the patient. The exception occurs when a small current is created for purposes of measuring basic electrical parameters such as the impedance between the dermal layer and an electrode, but such measurements are not generally considered as "active" signal development.

Several companies now market FDA approved NSM devices for clinical use. These devices provide a more direct and objective assessment of the degree of anesthesia based on the analysis of specific cranial bio-electrical measurements. This technology specifically detects and processes electroencephalographic (EEG) and electromyography (EMG) signals, commonly referred to as brain waves, and neuromuscular signals, to monitor changes in brain activity that is closely associated with various levels of anesthesia. The results of such brain wave analyses are typically presented in the form of a graphic display and a variable numerical value which provides an easily understood and objective representation of the patient's neurological state NSM systems are composed of one or more Electrode Assemblies connected to a Signal Processor Unit which is also connected to one or more Display Devices, as shown in FIG. 3.

While both NSM systems and EAS systems both provide advantages in different aspects of the general field of anesthesiology, these system are incompatible with each other. They cannot be operated simultaneously on the same individual person, because the actively produced signal produced by a EAS system interferes with the bio-signals monitored by NEM systems, such that the ability to obtain useful quantitative data from the bio-signal is substantially reduced. Accordingly, it has not been possible to use NSM systems to monitor the effect of EAS signals, and accurate monitoring of EAS systems has not been possible.

TABLE

Research Literature

1. Auriacombe M, Tignol J, Le Moal M, Stinus L: Transcutaneous electrical stimulation with Limoge current potentiates morphine analgesia and attenuates opiate abstinence syndrome, Biological Psychiatry, 15, 28 (8):650-656, 1990.
2. Dougherty P M, Dafny N: Transcranial electrostimulation attenuates the severity of naloxone-precipitated morphine withdrawal in rats, Life Sciences, 44:2051-2056, 1989.
3. Katsnelson IaS, Leosko V A: Evaluation of efficacy of new method of transcranial electroanalgesia in clinical anesthesiology, In: New Method of Transcranial Electroanalgesia, Abstracts of Scientific Conference, 20-22, 1987.
4. Krupitski E M, Burakov A M, Karandashova G F, Katsnelson IaS, Lebedev V P, Grinenko Aja, Borodkin JuS: The administration of transcranial electrical treatment for affective disturbances therapy in alcoholic patients, Drug and Alcohol Dependence, 27(1):1-6, 1991.
5. Lebedev V P, Airapetov L N, Katsnelson IaS, Savchenko A B, Petriaevskaia N V: Activation of antinociceptive system of the brain during transcranial electroanalgesia and the role of opioid and mediating mechanisms in the formation of this effect, In: New Method of Transcranial Electroanalgesia, abstracts of Scientific Conference, 12-14, Leningrad, 1987.
6. Lebedev V P, Savchenko A B, Petriaevskaia N V: The opiate mechanism of transcranial electroanalgesia in rats and mice, Fiziol Zh SSSR, 74(9):1249-1256, 1988.
7. Limoge A: An Introduction to Electroanesthesia. Baltimore: University Park Press: 120, 1975.
8. Limoge A, Robert C, Stanley T: Trancutaneous cranial electrical stimulation (TCES): A review 1998. Neuroscience and Behavioral Reviews, 23:529-538, 1999.
9. Mantz J, Azerad J. Limoge A, Desmonts J M: Transcranial electrical stimulation with Limoge's currents decreases halothane requirements in rats. Evidence for the involvement of endogenous opioids, Anesthesiology, 76(2):253-260, 1992.
10. Stanley T H, Gazalaa J A, Limoge A, Louville Y: Transcutaneous cranial electrical stimulation increases the potency of nitrous oxide in humans, Anesthesiology, 57:293-297, 1982 A.
11. Stanley T H, Gazalaa J A, Atinault A, Coeytaux R, Limoge A, Louville Y: Transcutaneous cranial electrical stimulation decreases narcotic requirements during neuroleptanesthesia and operation in man, Anesth Analg, 61:863-866, 1982 B.
12. Stinus L, Auriacombe M, Tignol J, Limoge A, Le Moal: Transcranial electrical stimulation with high frequency intermittent current (Limoge's) potentiates opiate-induced analgesia: blind studies, Pain, 42: 351-363, 1990.

SUMMARY OF INVENTION

An aspect of the present invention relates generally to generating analgesic effects for the augmentation of anesthesia by Electrical Anesthesia Stimulation (EAS). More particularly, it relates to methods of practicing the invention by concomitant operation of EAS in conjunction with certain methods of monitoring neurologic state.

The invention involves a system for reducing the requirements for anesthetic agents by allowing effective neurologic state monitoring concurrent with EAS. The system involves three main components;

(1) a Neurologic State Monitor (NSM) system adapted to passively monitor bio-electrical signals and produce quantitative values for the purpose of evaluating the degree of narcosis, analgesia, and areflexia of a person, (2) an Electrical Anesthesia Stimulation (EAS) system adapted to generate an EAS signal to potentiate the effect of anesthetic agents by stimulation of the thalamic area of the brain with repetitive electrical pulses, and (3) a Signal Interface Module (SIM) adapted to determine EAS signal interference artifacts in a bio-electrical signal monitored by the NSM system. The EAS signal interference artifacts are suppressed in the detected bio-electrical signals to produce a processed signal. The quantitative values produced by the NSM from the processed signal are used by the anesthesiologist to determine the person's neurological state.

"Person" as used in the specification and claims includes human beings, as well as mammals that react similarly to anesthetics. The invention is applicable in testing applications where animals are used, such as in medical trials, and to test anesthesiology and monitoring systems ultimately intended for humans. In addition, application of the invention is contemplated for veterinary systems for anesthetic treatment of large and small mammals.

This invention provides methods for the concomitant operation of two different systems supporting the practice of anesthesia, i.e., a EAS system and a NSM system. The innovations introduced by the invention produce a synergy that provides greater benefits with the two systems acting together than either would produce acting individually.

A purpose and value of this invention is to enhance the practice of anesthesia by significantly reducing the requirements for anesthetic agents during medical procedures while improving the quality and safety of the procedures and reducing the inherent risks that are associated with anesthesia. Practice of this invention should also significantly reduce the costs of anesthetic procedures and post-surgical care, with subsequent benefits for the health care system and the patients.

DETAILED DESCRIPTION

Description of the Invention

Issues Addressed by the Invention

Figure 1:
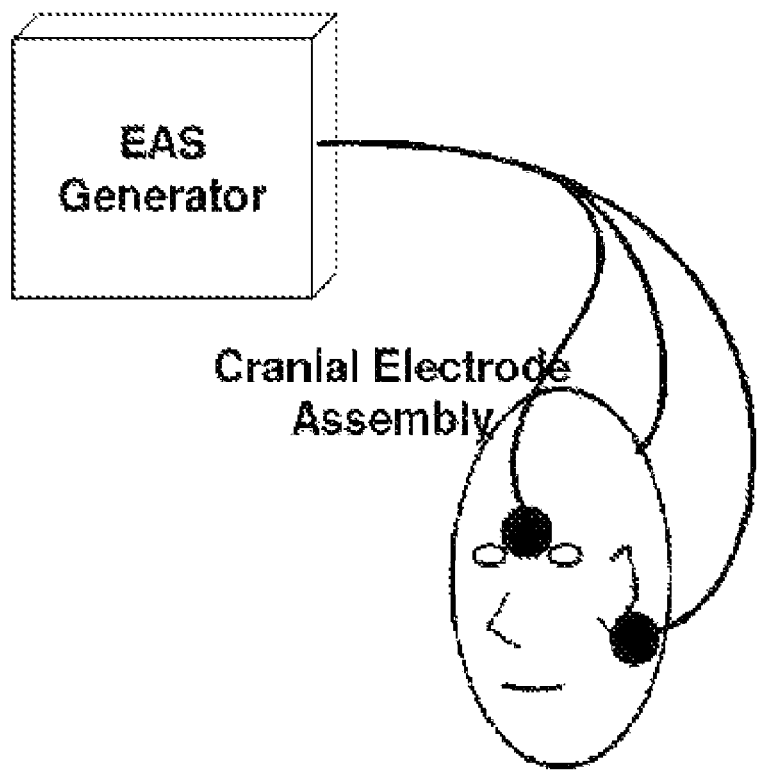
FIG. 1 is a schematic showing an EAS system with a cranial electrode assembly connected to a signal generator.

Issue 1: Objectivity, Specificity, and Precision in Anesthesia Assessment.

Conventional anesthesia practices require anesthesiologists to interpret relatively crude and indirect physiological variables, such as heart rate and systolic blood pressure, to assess a patient's neurological state. This does not facilitate the most accurate assessments of the level of anesthesia for determining the requirements for pharmacological agents needed to maintain a desired neurological state.

The specificity and precision of subjective variables and metrics used for anesthesia administration has direct significance on patient safety and well-being. Given that TCES enhances or extends the effects of anesthetic drugs and inhalants by 25% or more, the conventional practices and procedures for assessing and maintaining anesthesia may no longer suffice. Better tools for clinicians to determine the proper quantity of anesthetic agents and rates of delivery are needed to achieve the best clinical results.

Accurate monitoring of the neurological state is also a key issue for developing effective augmentation technologies such as TCES. Although it has the potential to greatly enhance the practice of anesthesia, EAS acceptance is limited by the lack of specificity and precision in the variables and metrics used for clinical decisions regarding anesthesia maintenance. Improvements in the methods used to assess neurological state are required in order to advance the practice of anesthesia. The apparent effectiveness of enabling technologies such as TCES is currently limited by the clinician's ability to quickly and accurately interpret data that signals changes in levels of neurological state.

Methods for the concomitant operation of NSM in conjunction with TCES are described herein that effectively resolve this issue.

Issue 2: Active Signal Interference with Passive Monitoring Systems.

Signal interference is a significant technical issue when active signal generators, such as TCES, are used in conjunction with passive signal detection devices such as NSM equipment. The signals produced by any EAS device will be significantly stronger than the brain's bio-electrical signals detected by NSM electrodes on the surface of the scalp and skin. The potential for interference becomes even greater when the electrodes from each device are located near each other—which is generally the case. For instance, both systems usually require electrodes placed on the forehead. For an optimal embodiment of this invention it may be desirable to collocate some electrodes, or to use certain individual electrodes to both send and receive signals for the respective systems.

Even though modern NSM systems employ certain methods to reject interference signal artifacts, it is highly desirable to ensure that TCES signal interference issues are properly resolved in the practical embodiment of the invention and, indeed, innovative methods are described herein to efficiently resolve this issue.

Issue 3. Reducing the Risks and Cost of Anesthesia

Any surgical procedure requiring anesthesia has inherent risks. It is known that the adverse effects of anesthetic agents on the human body are increased by the quantity of the agents administered to patients. Over-medication during anesthesia is considered quite serious since vital processes, such as respiratory function, may cease under deep states of consciousness. This is one of the primary reasons for the development of NSM systems. On the other hand, under-medication is also very serious since patients may inadvertently remain conscious while in a state of paralysis and be fully aware of the medical procedure being performed on them. The ultimate goal of an anesthesiologist is to administer "just enough" pharmacological agents to achieve and safely maintain the required neurological state during a medical procedure.

Anesthesia is also costly. Beyond the high cost of anesthetic agents is the cost of post-operative care, which is also influenced by the amount of anesthetic medications used on the patient. Patients that are over or under-medicated during anesthesia require additional attention and support during and following surgery, thereby increasing the costs associated with the procedure.

The practices of this invention in the several embodiments described herein should significantly reduce the risks and costs of anesthetic procedures.

Examples of various aspects of the invention are described herein. Illustrated is a method of concurrently operating a passive NSM component with an active EAS component to enhance anesthesia results. The invention also permits both components to operate concurrently without the active stimulation device introducing interference artifacts in the passive signal detection system.

An aspect of the invention comprises a NSM System component (NSM Subsystem), a EAS System component (EAS Subsystem) and a Signal Interface Module (SIM).

Suitable NSM and EAS subsystem components include existing prior art technologies that are enabled for concurrent operation by the innovations of the Signal Interface Module.

Due to the amplitude of the EAS signal and the approximate collocation of cranial electrodes used by the NSM and EAS subsystems, EAS signal contamination of bio-signals detected by the NSM subsystem is a concern. Artifacts in the NSM produced by EAS signal contamination could result in erroneous NSM indications and thereby adversely affect the safety and quality of medical procedures. The purpose of the Signal Interface Module is to facilitate concurrent operation of the active EAS subsystem with the NSM subsystem while preventing the creation of signal interference artifacts in the passive NSM subsystem that could produce erroneous NSM results.

Examples of the Invention

Below are examples of two general embodiments of the present invention. The first general embodiment is referred to as the Discrete Signal Interface (DSI) embodiment. In this embodiment the TCES system and the NSM system are separate and discrete stand-alone devices that might be commercially available off the shelf. These stand alone TCES and NSM systems are then interconnected through the SIM. When the discrete TCES and NSM systems are then interconnected through the SIM, they then become subsystems, known as the EAS Subsystem and the NSM Subsystem, of the invention. The purpose of the SIM is to facilitate concurrent and concomitant operation of both the EAS and NSM Subsystems.

Figure 4:
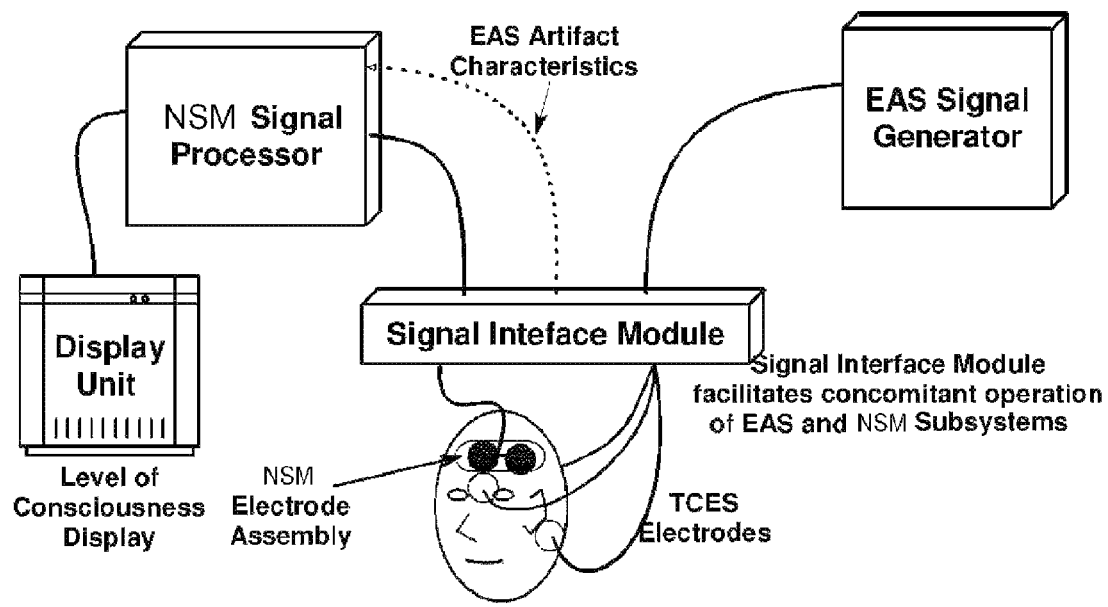
FIG. 4 is a schematic block diagram showing an aspect of the invention.

The second general embodiment is the Consolidated Device Configuration (CDC) embodiment. In this embodiment the invention's three subsystems are manufactured within a common housing and may share certain other common elements such as power supplies and processing circuitry. This is a preferred embodiment of the invention. A functional block diagram of the invention in its general, non-specific, embodiment with the major subsystems is shown in FIG. 4.

EAS Subsystem

Any system for generating an EAS signal that creates an signal that augments or potentiates the effect of anesthesia substances is contemplated by the invention. In particular, the EAS systems described above in the section "Transcutaneous Cranial Electrical Stimulation (TCES)" have been found suitable for practice of the invention. Other EAS systems have been disclosed in the prior-art, some based upon principles discussed in the above section. Whilenot all of these EAS systems have been shown effective in actual practice, they may be incorporated in the present invention where they do provide an effective EAS signal. Prior-art EAS systems are disclosed in the following United States Patents:

U.S. Pat. No. 6,161,044, Silverstone, Dec. 12, 2000, "Method And Apparatus For Treating Chronic Pain Syndromes, Tremor, Dementia And Related Disorders And For Inducing Electroanesthesia Using High Frequency, High Intensity Transcutaneous Electrical Nerve Stimulation"

U.S. Pat. No. 6,567,702, Nekhendzy, et al., May 20, 2003, "Eliciting Analgesia By Transcranial Electrical Stimulation"

U.S. Pat. No. 6,904,322, Katsnelson, Jun. 7, 2005, "Transcranial Electrostimulation Apparatus And Method"

U.S. Pat. No. 6,505,079, Foster, et al., Jan. 7, 2003, "Electrical Stimulation Of Tissue For Therapeutic And Diagnostic Purposes"

EAS Subsystem as Represented by TCES

TCES is a well documented example of EAS prior art for the augmentation of anesthesia. It is a method developed for potentiating pharmacological anesthesia effects by active electrical stimulation of certain areas of the brain. TCES allows effective anesthesia to be maintained with reduced drug requirements after pharmacological induction, resulting in significant patient benefits and reduced expenses for anesthetic agents. Although specific details may vary, TCES signal characteristics and mechanisms of action are similar in nature to those of other EAS devices and systems found in the medical literature and in clinical practice. Additionally, brief periodic interruptions (e.g., tens of millisecond interruptions every second or so) of TCES, or other EAS systems, signals are not expected to interfere with the anesthesia augmentation effect.

Figure 2:
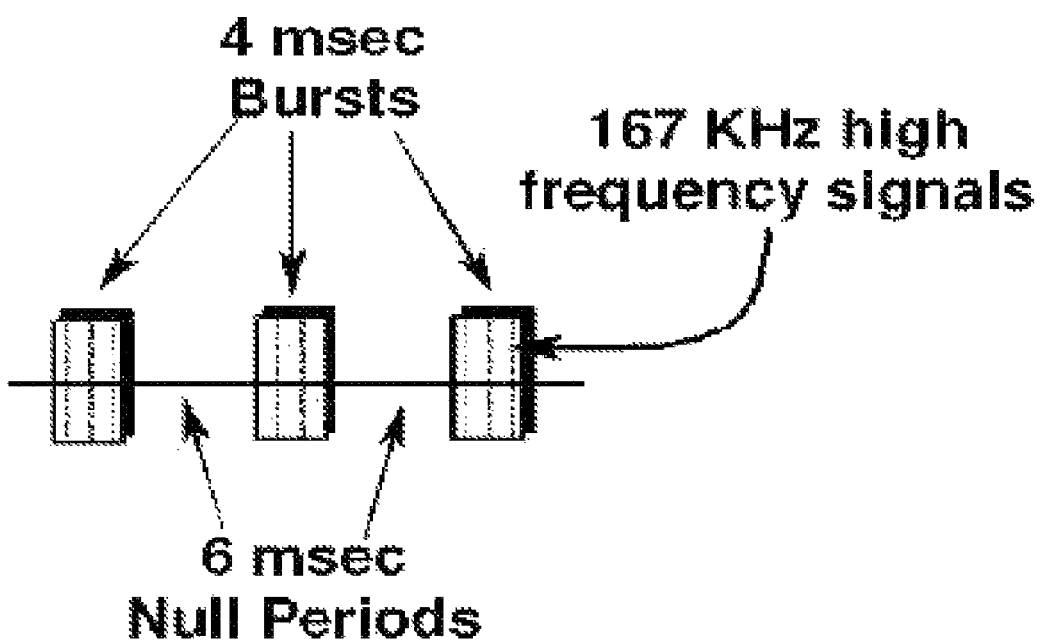
FIG. 2 is a schematic showing characteristics of a TCES signal and EAS signal timing.
Figure 3:
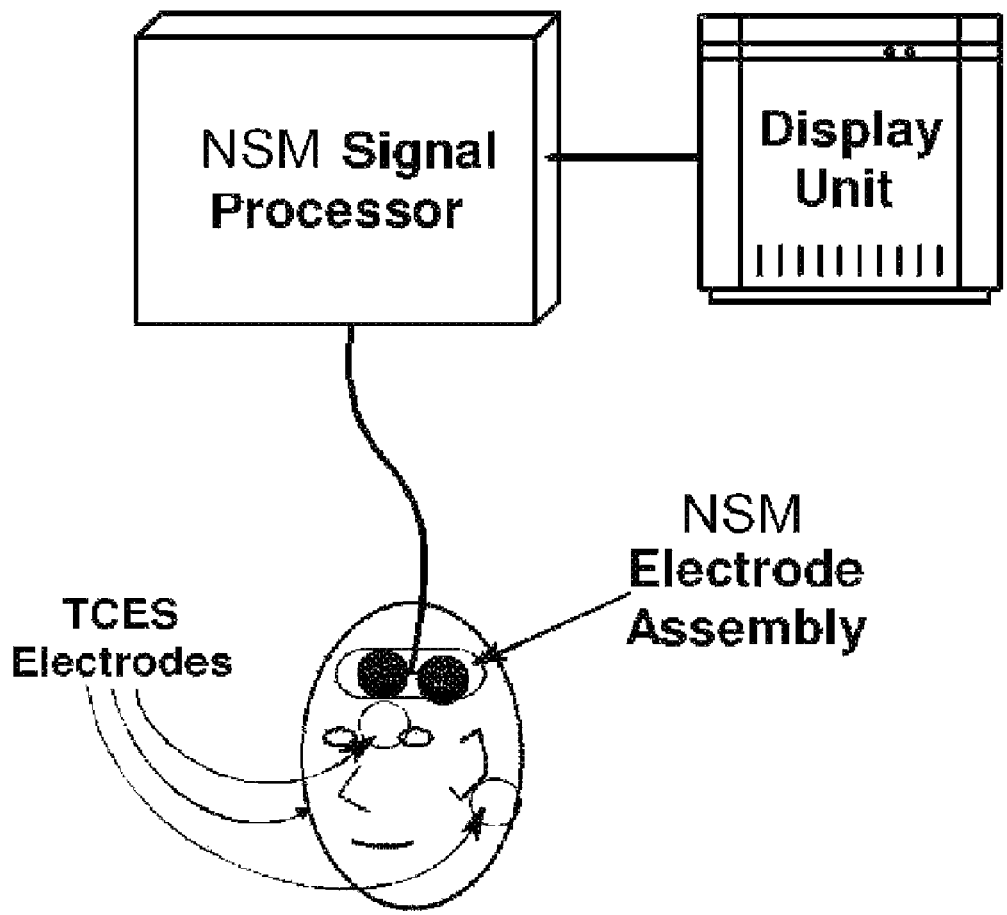
FIG. 3 is a schematic of a NSM system showing electrode assemblies connected to signal processor connected to a display device.

In a specific example, the principal electrical characteristics of a TCES signal are a high frequency (167 kHz) biphasic signal component gated by a 100 Hz asymmetrical low frequency component that breaks the high frequency signal into 4 msec bursts with each burst followed by a 6 msec null signal period, as shown in FIG. 2.

TCES signals are electrically transmitted through the cranium by two electrodes placed behind the ears and one electrode on the forehead. The three electrodes are collectively called the EAS Electrode Assembly and may be configured as shown in FIG. 1.

Signal frequencies and timing parameters vary somewhat between different EAS devices, as does the specific locations of cranial electrode placement. TCES may be considered exemplary of various EAS systems for purposes of this discussion. The practice of this invention may be implemented with almost any suitable EAS system in at least one or more of its embodiments.

Passive NSM Subsystem

Neurological state monitoring systems employ the processing and analysis of EEG signals and other bio-electrical measurements to determine the "neurological state" of anesthetized patients. Such systems offer measurements related to specific brain activity, providing anesthesiologists with direct quantitative and objective metrics that can be used effectively by clinicians, in conjunction with other conventional physiological signals and measures, to facilitate precise administration and control of the patient's anesthesia state. This can enhance patient safety and reduce the amount and cost of anesthetic agents required for medical procedures.

Specifics of the NSM technology are not relevant to this invention nor to discussions of its embodiments provided the NSM system employs EEG and similar bio-electrical signals to accurately determine and display neurological state information suitable for use by the anesthesiologist.

Suitable NSM systems that are contemplated by the invention include, but are not limited to, those disclosed in the following United States Patents U.S. Pat. No. 6,801,803, Viertio-Oja, Oct. 5, 2004, "Method And Apparatus For Determining The Cerebral State Of A Patient With Fast Response"

U.S. Pat. No. 6,757,558, Lange, et al., Jun. 29, 2004, "Objective Pain Measurement System And Method"

U.S. Pat. No. 5,458,117, Chamoun, et al., Oct. 17, 1995, "Cerebral Biopotential Analysis System"

A preferred NSM Subsystem is characterized by any of several commercially available systems. These systems usually have the following characteristics:

(1) The NSM system passively monitors and analyzes several different EEG signals from the brain, optionally including bio-electrical parameters, to characterize the neurological state of a patient. Exemplary systems typically employ sophisticated signal processing methods involving Fourier analysis and other time and spectrum methods of signal processing.

(2) NSM signal processing also includes artifact suppression functions.

(3) NSM is characterized by sampling specific EEG frequency spectra, or bio-electrical measurements (e.g., transdermal impedance), at specific cranial locations using several electrodes comprising a NSM Electrode Assembly.

(4) NSM electrodes are attached to the skin by adhesive compounds or by an Electrode Assembly that physically holds each electrode firmly in place. Specific electrode attachment locations will vary somewhat depending on the manufacturer and the type of NSM system being used.

(5) EEG signal samples are taken from the several NSM electrodes at rates varying from approximately several samples per second to over several hundred samples per second.

EEG and other bio-electrical signals and measurements are processed in one or more ways, which may be proprietary to a particular manufacturer of NSM systems, to provide the neurological state data displayed for the clinician.

Signal Interface Module

The Signal Interface Module (SIM) facilitates concurrent operation of the active EAS subsystem with the NSM subsystem while reducing or eliminating EAS signal interference artifacts in the passive NSM Subsystem. When used in the general DSI embodiment, there may be several different versions of the SIM that can be used, each designed to specifically operate with a particular EAS and NSM system. The SIM may exist as a separate module, or be suitably incorporated or integrated into any other module, system, or circuitry.

A suitable Signal Interface Module includes several functions. An exemplary Signal Interface Module may contain the following components to accomplish these functions. A Signal Interface Module can include any arrangement of components that fills the functions described below.

The components of the exemplary Signal Interface Module include:

(1) Subsystem Interface

The subsystem interface includes five components:

(a) NSM Cable Interface, which facilitates the electrical connections to the NSM Signal Processor Unit (b) TCES Cable Interface, which facilitates the electrical connections to the EAS Signal Generator Unit (c) NSM Electrode Assembly Interface, which facilitates the electrical connections to the NSM Electrode Assembly.

(d) TCES Electrode Assembly Interface, which facilitates the electrical connections to the TCES Electrode Assembly (e) Display component with control switch to activate the unit and indicate its status.

(2) Signal Discrimination Processor (SDP)

The Signal Discrimination Processor has the function of suppressing or eliminating any EAS signal artifacts that might interfere with NSM signal processing. It has several different embodiments. These embodiments may be employed separately or they may be combined to use the desired features and capabilities of two or more embodiments. The invention contemplates any suitable system of for the SDP to suppress EAS artifacts.

(a) Signal-Time Multiplexing

This system determines and suppresses the EAS signal artifacts by restricting most NSM sampling to the intervals occurring between active high frequency EAS signals. This is called Signal-Time Multiplexing because active EAS signals and passive NSM signal sampling are interleaved over time.

Using the TCES example, this would involve taking NSM signal samples during the 6 msec intervals between TCES high frequency signal bursts. For example, if the NSM collects samples at a rate of 250 samples per second, a period of 4 msec is needed to collect one sample. This indicates that at least 1 sample can be easily be taken in the 6 msec period between each TCES high frequency burst. The NSM therefore can collect at least 100 interference-free samples per second.

This approach may lower the NSM data collection rate somewhat, and it may not be suitable for use with some NSM devices. However, in the general Consolidated Device Configuration embodiment the NSM Signal Processor component could be designed specifically for sampling with the Signal Time Multiplexing system.

An alternative version of Signal Time Multiplexing might be required when the EAS signal is continuous or does not have a sufficiently long null period to support NSM sampling. In this case the EAS signal might be periodically interrupted for brief intervals by the Signal interface Module to permit interference free NSM sampling.

Brief periodic interruptions of EAS signals, for no more than a few seconds two or three times per minute, are not expected to interfere with the anesthesia augmentation effect of EAS. This approach is technically feasible, but it is also not very suitable for the Discrete Signal Interface general embodiment of the invention.

(b) Pre-Processed Signal Discrimination

Figure 5:
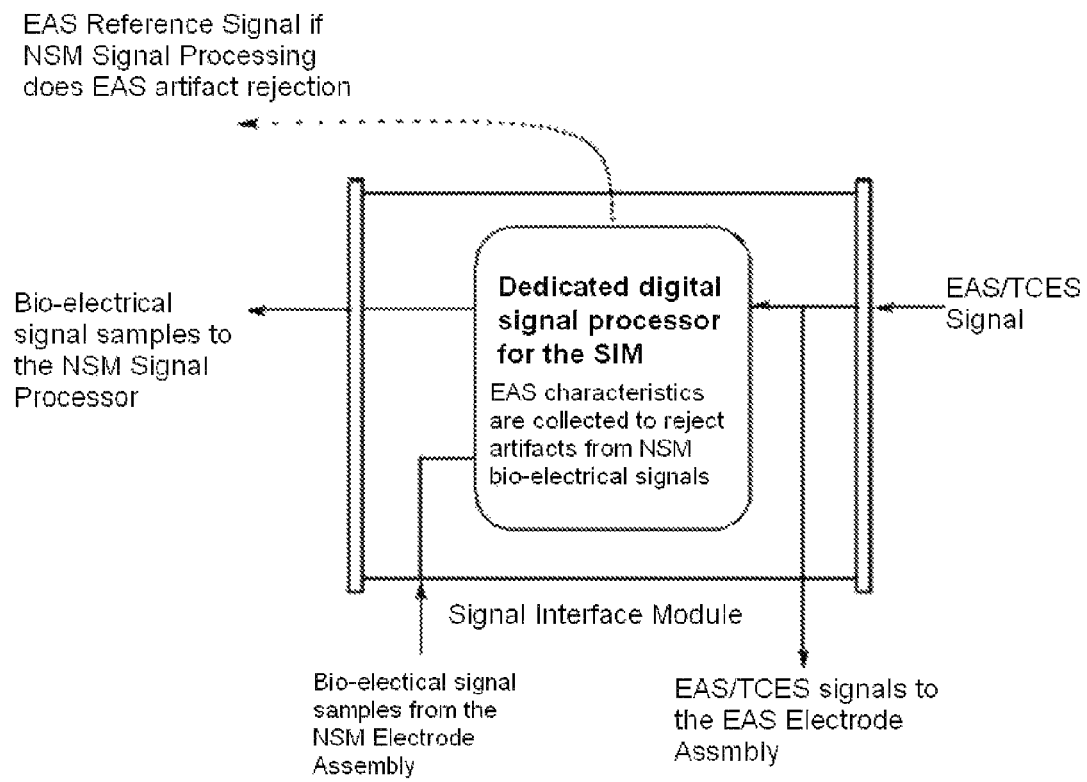
FIG. 5 is a block diagram showing pre-processed signal discrimination.

This approach involves adapting the NSM Signal Processor, or a providing a similar dedicated signal processor in the SIM, to identify and reject EAS signal artifacts from the bio-electrical signal information passed to the NSM processing system. This method is easily understood when it is realized that EAS signals are well defined and repetitive, therefore they exhibit unique time and frequency characteristics. The EAS signal can be analyzed with great precision in mathematical terms by time and spectral analysis. The processor uses the EAS signal characteristics to detect artifacts and extract them from NSM signals during normal NSM signal processing. In effect, the Signal Processor is given very specific information about EAS by the SIM so that it knows precisely what to look for and reject. This process is depicted in FIG. 5.

Pre-Processed Signal Discrimination is part of the a preferred embodiment for the invention when used in a Consolidated Device Configuration.

(c) Reconstituting Lost Signal Portions

Figure 6:
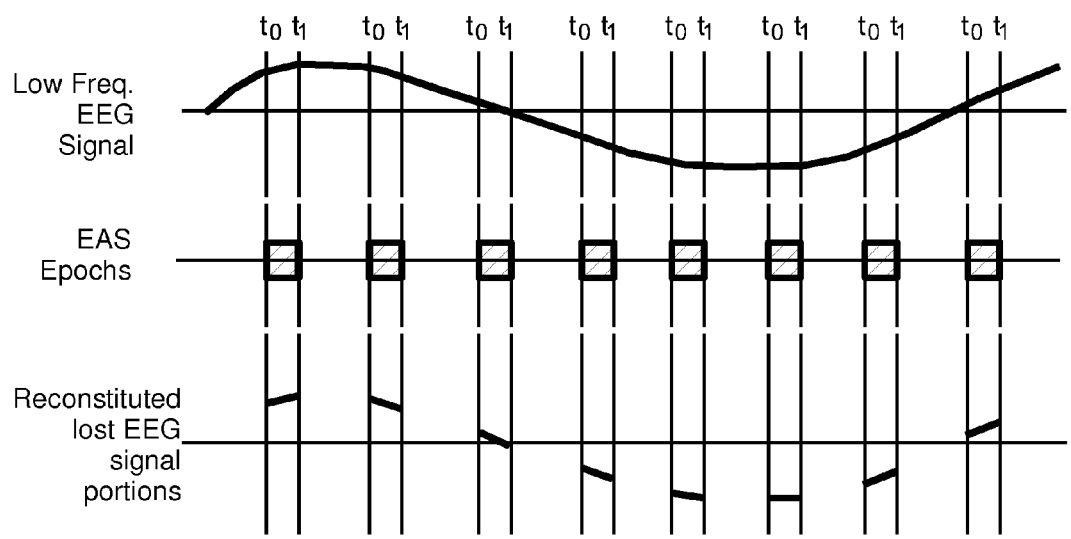
FIG. 6 is a graph showing a lost signal reconstitution.

This approach involves determining and suppressing the EAS signal interference artifices by deleting portions from the low frequency EEG signal where they correspond to EAS epochs. An EAS epoch is where the processor in the EAS signal generator is generating an EAS pulse, i.e., creating a non-zero value in the signal. During this epoch the EEG signal is deleted, and reconstituted or replaced by substitute signal. The substitute signal is derived from signal values on either side of the delete portion, for example at the start of the deleted portion $f_0$ and the end of the deleted portion, $f_1$. Referring to FIG. 6, several mathematical algorithms could be used to generate a substitute signal, but the three simplest include; (1) using the start value ($f_0$) for the entire substitute signal (i.e. sample and hold), (2) use an average value of the start value ($f_0$) and end value ($f_1$), and (3) use a linear or non-linear function between the start value ($f_0$) and end value ($f_1$).

Where the EAS epochs are located on the signal time-line are those portions were the EAS signal artifacts occur. Accordingly, by deleting and reconstituting these portions, the EAS signal artifacts are determined and suppressed from the EEG signal. Referring to FIG. 6, is shown reconstitution showing a linear reconstitution between the start and end points.

While this invention has been described with reference to certain specific embodiments and examples, it will be recognized by those skilled in the art that many variations are possible without departing from the scope and spirit of this invention, and that the invention, as described by the claims, is intended to cover all changes and modifications of the invention which do not depart from the spirit of the invention.

The TCES system used herein to describe this invention is not meant to be an exclusive component or limitation of the invention. TCES is used to as a representative example of a viable EAS system with the ability to enhance anesthesia by reducing the requirements for anesthetic agents.

The practice of this invention may be implemented in one or more of its embodiments, individually or in combination, with any EAS system that employs transcutaneous cranial electrical stimulation to support and enhance pharmacological anesthesia. This flexibility also applies to NSM systems that meet the basic criteria used in this discussion to characterize NSM.

What is claimed is:

1. An apparatus for passive monitoring of bioelectric signals in the presence of active electrical anesthesia stimulation, the apparatus comprising:
   a Neurological State Monitoring (NSM) system adapted to passively monitor bio-electrical signals
   an Electrical Anesthesia Stimulation (EAS) system adapted to actively generate an EAS signal to potentiate anesthetic agents by brain stimulation of the person with repetitive electrical pulses,
where the EAS signal creates EAS interference artifacts upon the monitored bio-electric signal:
   a Signal Interface Module (SIM) adapted to determine EAS signal interference artifacts in the monitored bio-electrical signal monitored by the NSM system
   where the EAS signal interference artifacts are suppressed in the detected bio-electrical signal to produce a processed bio-electrical signal that can be used to produce quantitative values for evaluating neurological state,
the detected interference artifacts determined and suppressed by operating the NSM system to monitor the bio-electrical signal during time intervals where the EAS signal has a null value.

2. An apparatus as in claim 1 wherein the bio-electric signal can be used to produce quantitative values for evaluating any one of or any combination of narcosis, analgesia, and areflexia.

3. An apparatus as in claim 1 wherein the detected interference artifacts are determined and suppressed by the NSM system based upon a reference signal generated by the SIM.

4. An apparatus as in claim 1 wherein multiple bio-electrical signals are monitored by the NSM system and EAS signal interference artifacts are detected in each of these signals by the SIM.

5. An apparatus as in claim 1 wherein the NSM system, EAS system, and SIM are consolidated into a single system.

6. An apparatus as in claim 1 wherein the NSM system, EAS system, and SIM are separate components connected by suitable signal transfer conductors.

7. An apparatus for passive monitoring of bioelectric signals in the presence of active electrical anesthesia stimulation, the apparatus comprising:
   a Neurological State Monitoring (NSM) system adapted to passively monitor bio-electrical signals
   an Electrical Anesthesia Stimulation (EAS) system adapted to actively generate an EAS signal to potentiate anesthetic agents by brain stimulation of the person with repetitive electrical pulses,
where the EAS signal creates EAS interference artifacts upon the monitored bio-electric signal;
   a Signal Interface Module (SIM) adapted to determine EAS signal interference artifacts in the monitored bio-electrical signal monitored by the NSM system
   where the EAS signal interference artifacts are suppressed in the detected bio-electrical signal to produce a processed bio-electrical signal that can be used to produce quantitative values for evaluating neurological state,
the detected interference artifacts determined and suppressed by comparing the signal generated by the SIM and the bio-signal monitored by the NSM system and suppressing artifacts from the generated signal from the monitored bio-signal.

8. An apparatus as in claim 7 wherein the bio-electric signal can be used to produce quantitative values for evaluating any one of or any combination of narcosis, analgesia, and areflexia.

9. An apparatus as in claim 7 wherein the detected interference artifacts are determined and suppressed by the NSM system based upon a reference signal generated by the SIM.

10. An apparatus as in claim 7 wherein multiple bio-electrical signals are monitored by the NSM system and EAS signal interference artifacts are detected in each of these signals by the SIM.

11. An apparatus as in claim 7 wherein the NSM system, EAS system, and SIM are consolidated into a single system.

12. An apparatus as in claim 7 wherein the NSM system, EAS system, and SIM are separate components connected by suitable signal transfer conductors.

13. An apparatus for passive monitoring of bioelectric signals in the presence of active electrical anesthesia stimulation, the apparatus comprising;
   a Neurological State Monitoring (NSM) system adapted to passively monitor bio-electrical signals;
   an Electrical Anesthesia Stimulation (EAS) system adapted to actively generate an EAS signal to potentiate anesthetic agents by brain stimulation of the person with repetitive electrical pulses,
where the EAS signal creates EAS interference artifacts upon the monitored bio-electric signal;
   a Signal Interface Module (SIM) adapted to determine EAS signal interference artifacts in the monitored bio-electrical signal monitored by the NSM system
   where the EAS signal interference artifacts are suppressed in the detected bio-electrical signal to produce a processed bio-electrical signal that can be used to produce quantitative values for evaluating neurological state,
the detected interference artifacts determined and suppressed by deleting portions of the bio-signal monitored by the NSM system that correspond to periods when the EAS system is generating a non-zero EAS signal.

14. An apparatus as in claim 13 wherein the bio-electric signal can be used to produce quantitative values for evaluating any one of or any combination of narcosis, analgesia, and areflexia.

15. An apparatus as in claim 13 wherein the detected interference artifacts are determined and suppressed by the NSM system based upon a reference signal generated by the SIM.

16. An apparatus as in claim 13 wherein multiple bio-electrical signals are monitored by the NSM system and EAS signal interference artifacts are detected in each of these signals by the SIM.

17. An apparatus as in claim 13 wherein the NSM system, EAS system, and SIM are consolidated into a single system.

18. An apparatus as in claim 13 wherein the NSM system, EAS system, and SIM are separate components connected by suitable signal transfer conductors.

19. A method for passive monitoring of bioelectric signals in the presence of active electrical anesthesia stimulation, the method comprising:
  passively monitoring bio-electrical signals;
  actively generating an Electrical Anesthesia Stimulation (EAS) signal to potentiate anesthetic agents by brain stimulation of the person with repetitive electrical pulses,
where the EAS signal creates EAS interference artifacts upon the monitored bio-electric signal;
  determining EAS signal interference artifacts in the monitored bio-electrical signal;
  where the EAS signal interference artifacts are suppressed in the detected bio-electrical signal to produce a processed bio-electrical signal that can be used to produce quantitative values for evaluating neurological state,
the detected interference artifacts determined and suppressed by monitoring the bio-electrical signal during time intervals where the EAS signal has a null value.

20. A method as in claim 19 wherein the bio-electric signal can be used to produce quantitative values for evaluating any one of or any combination of narcosis, analgesia, and areflexia.

21. An apparatus as in claim 19 wherein multiple bio-electrical signals are monitored and EAS signal interference artifacts are detected in each of these signals.

22. A method as in claim 19 wherein
  A method for passive monitoring of bioelectric signals in the presence of active electrical anesthesia stimulation, the method comprising:
  passively monitoring bio-electrical signals;
  actively generating an Electrical Anesthesia Stimulation (EAS) signal to potentiate anesthetic agents by brain stimulation of the person with repetitive electrical pulses,
  where the EAS signal creates EAS interference artifacts upon the monitored bio-electric signal;
  determining EAS signal interference artifacts in the monitored bio-electrical signal;
  where the EAS signal interference artifacts are suppressed in the detected bio-electrical signal to produce a processed bio-electrical signal that can be used to produce quantitative values for evaluating neurological state,
  the detected interference artifacts determined and suppressed by comparing the generated EAS signal generated and the monitored bio-signal and suppressing artifacts from the generated signal from the monitored bio-signal.

23. A method as in claim 22 wherein the bio-electric signal can be used to produce quantitative values for evaluating any one of or any combination of narcosis, analgesia, and areflexia.

24. An apparatus as in claim 22 wherein multiple bio-electrical signals are monitored and EAS signal interference artifacts are detected in each of these signals.

25. A method as in claim 19 wherein
  A method for passive monitoring of bioelectric signals in the presence of active electrical anesthesia stimulation, the method comprising:
  passively monitoring bio-electrical signals;
  actively generating an Electrical Anesthesia Stimulation (EAS) signal to potentiate anesthetic agents by brain stimulation of the person with repetitive electrical pulses,
  where the EAS signal creates EAS interference artifacts upon the monitored bio-electric signal;
  determining EAS signal interference artifacts in the monitored bio-electrical signal;
  where the EAS signal interference artifacts are suppressed in the detected bio-electrical signal to produce a processed bio-electrical signal that can be used to produce quantitative values for evaluating neurological state,
  the detected interference artifacts determined and suppressed by deleting portions of the monitored bio-signal that correspond to periods when a non-zero EAS signal in being generated.

26. A method as in claim 25 wherein the bio-electric signal can be used to produce quantitative values for evaluating any one of or any combination of narcosis, analgesia, and areflexia.

27. An apparatus as in claim 25 wherein multiple bio-electrical signals are monitored and EAS signal interference artifacts are detected in each of these signals.

\* \* \* \* \*